United States Patent [19]

Meyer et al.

[11] Patent Number: 4,482,246

[45] Date of Patent: Nov. 13, 1984

[54] INDUCTIVELY COUPLED PLASMA DISCHARGE IN FLOWING NON-ARGON GAS AT ATMOSPHERIC PRESSURE FOR SPECTROCHEMICAL ANALYSIS

[76] Inventors: Gerhard A. Meyer, 2446 Ginter La., Midland, Mich. 48640; Ramon M. Barnes, 109 Mount Warner Rd., Hadley, Mass. 01035

[21] Appl. No.: 420,681

[22] Filed: Sep. 20, 1982

[51] Int. Cl.³ ............................................. G01N 21/73
[52] U.S. Cl. ........................... 356/316; 219/121 PM; 219/121 PN; 219/121 PQ; 313/231.31; 315/111.51
[58] Field of Search .................... 356/316; 219/121 P, 219/121 PM, 121 PN, 121 PP, 121 PQ, 121 PU, 121 PT; 313/231.31; 315/111.21, 111.51

[56] References Cited

U.S. PATENT DOCUMENTS

Re. 29,304  7/1977  Greenfield et al. ................. 356/316
4,266,113  5/1981  Denton et al. ............... 219/121 PM

OTHER PUBLICATIONS

Scott et al., "Inductively Coupled Plasma-Optical Emission Analytical Spectrometry", Anal. Chem., vol. 46, No. 1, pp. 75-80, Jan. 1974.
Allemand et al., "A Study of Inductively Coupled Plasma Torch Configurations", Applied Spectroscopy, vol. 31, No. 5, 1977, pp. 434-443.
Barnes et al., "Low-Power Inductively Coupled Nitrogen Plasma Discharge for Spectrochemical Analysis", Anal. Chem. 1980, 52, 1523-1525.
Fassel et al., Anal. Chem., vol. 37, No. 7, Jun. 1965, p. 921.
Boumans et al., Spectrochemical Acta, 30B, pp. 312-315, 1975.
Greenfield et al., Anal. Chim., 74, 233-236, 1975.

Primary Examiner—F. L. Evans

[57] ABSTRACT

Disclosed is a novel apparatus for the production of a sustained inductively coupled non-argon plasma discharge in flowing gas in a 13-25 mm (analytical size) containment tube at atmospheric pressure. The apparatus is developed for elemental analysis of injected aerosol or powdered samples, and particularly for air monitoring applications.

10 Claims, 3 Drawing Figures

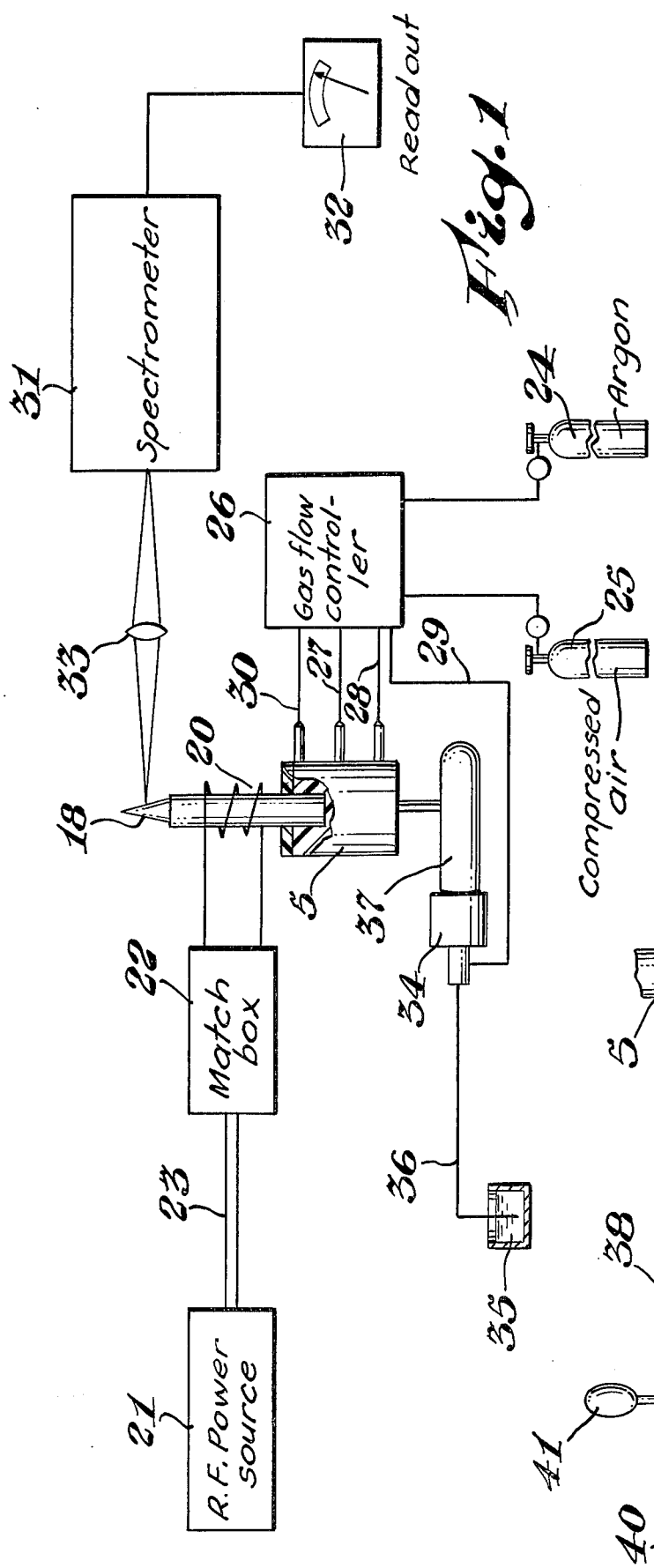
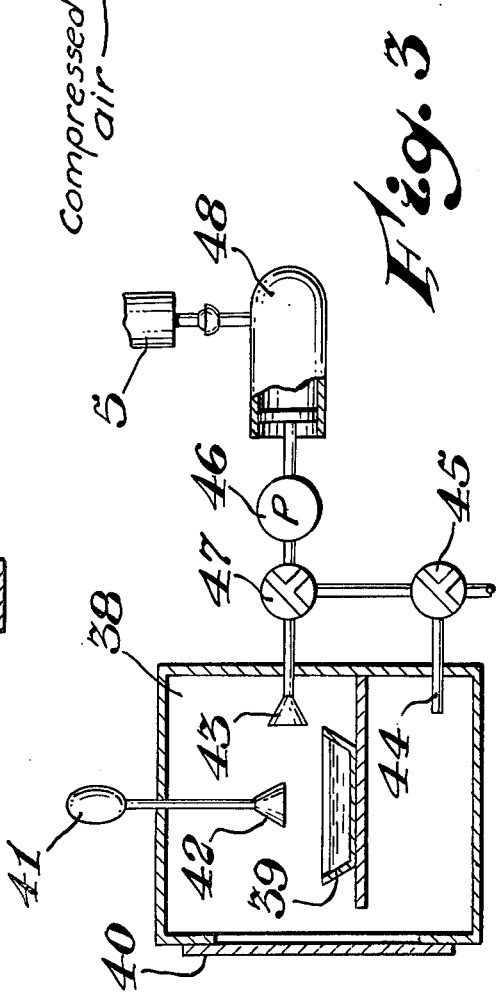

INDUCTIVELY COUPLED PLASMA DISCHARGE IN FLOWING NON-ARGON GAS AT ATMOSPHERIC PRESSURE FOR SPECTROCHEMICAL ANALYSIS

BACKGROUND OF THE INVENTION

A plasma discharge, sometimes called a "high pressure plasma" is a gas which at high enough temperature (above 5000 K) becomes luminous and electrically conducting. These discharges are conventionally formed in electric arcs. Whereas the electrodes used to produce these plasma discharges are generally well cooled, they are nevertheless subject to chemical and thermal erosion from the reactive hot gases produced in an arc. This severely reduces electrode lifetime and arc stability.

In 1961, Reed, J. Appl. Physics 32, 821, first reported an atmospheric pressure electrical discharge produced without using electrodes by inductively heating a gas with high frequency electrical energy. This culminated a long history of experimentation with high frequency heating of low pressure gases. This discovery was later patented (U.S. Pat. No. 3,324,334). Shortly thereafter two more patents were granted (U.S. Pat. Nos. 3,467,471 and 3,521,959) for inventions first disclosing such a plasma discharge for use in optical emission spectroscopy for chemical analysis. Since 1964 the inductively coupled plasma (ICP) has been researched extensively as a source for optical emission spectroscopy in the laboratory and since 1975 has been accepted as a viable commercial tool for elemental analysis.

Owing to the ease of operation and desirable spectrochemical properties, ICP discharges for elemental analysis are now commonly operated at atmospheric pressure with argon, or a combination of argon and nitrogen, air, or oxygen. For these latter ICP discharges, argon supports the discharge and "coolant" nitrogen or other diatomic gas prevents the hot discharge from damaging the container walls.

In contrast to these diatomic gas-argon ICP discharges, no reports or patents are known to have previously appeared disclosing an inductively coupled non-argon plasma discharge (defined hereinafter) for spectrochemical analysis. Operation of a total air ICP, e.g., with a compressor used to supply the air results in an attractive reduction in operation costs for the gas supply and offers the convenience of never running out of tank gas. In terms of detection capabilities, the total air ICP has been found to be equal to or superior to the total argon ICP for the determination of calcium, for example. This indicates that for the analysis of calcium or other elements having similar ionization potentials, the air ICP can be used as a viable alternative to the argon ICP at a substantial reduction in operating costs.

TERMS

"Configuration factor" is a critical ratio for the purpose of the invention determined by dividing the O.D. of the intermediate tube, measured adjacent its upper terminal edge portion, by the I.D. of the plasma containment tube, as measured in the same vicinity.

"Non-argon plasma discharge" means an inductively coupled plasma discharge sustained using flowing non-argon plasma gas and non-argon carrier gas; and which is further defined as not being composed of substantial plasma gas generated by ablation of tube surface components.

"Non-argon plasma gas" means a generally pure gas other than argon, or a mixture of gases not containing substantial argon, which is fed to the inner annulus (between the nebulizer and intermediate tube), and which is useful to sustain a non-argon plasma discharge using the apparatus of the invention. Illustrative of non-argon plasma gases which may be advantageously selected for employment according to the invention include, e.g., the gas mixture air; and as further non-limiting examples, readily available and inexpensive molecular gases such as oxygen, nitrogen, or carbon dioxide.

"Non-argon coolant gas" means a generally pure gas other than argon or a mixture of gases not containing substantial argon fed to the outer annulus, (adjacent the containment tube) and which is not incompatible with the non-argon plasma gas when used in the practice of the invention. Normally, the non-argon plasma gas and non-argon coolant gas will be the same, and supplied at separately controlled flow rates from the same compressed gas cylinder (or air compressor, as applies).

"Carrier gas" means and refers to the gas used to disperse the sample in the plasma discharge and is a gas or gas mixture compatible for such use; and preferably comprises the same gas or gas mixture as the non-argon plasma gas and non-argon coolant gas.

"Vessel" means and refers to any vessel, not limited in geometry, but most typically a cylinder, which contains a retrievable gas under compression and/or which contains a gas retrievable for the purposes of the invention, e.g., by gas generation or other mechanism, such as by heating a liquid or solid.

"Tube" as used to describe the containment, intermediate, and central tubes does not in the revelant art terminology strictly and literally refer only to cylinders; and this is the meaning also intended in this specification, but only so far as any departure from cylinder geometry is not detrimental to the purposes of the invention. In respect to the claim recitations regarding the torch design generally, and except for the critical configuration factor recited, the inventors hereby state their intention to rely on the Doctrine of Equivalents to determine the reasonable and fair scope of the invention claimed.

"Scott and Greenfield torch configurations" refer to specific prior art plasma torches of three concentric tubes of the dimensions 18-16-6 (Scott configuration) and 25-22-6 (Greenfield configuration) wherein the numbers refer to the inner diameter of the containment tube, and outer diameters of the remaining two tubes in millimeters. These prior art designs are similar to that used in the apparatus of the claimed invention, except for the modification of the critically recited configuration factor, above.

STATEMENT OF THE INVENTION

Specifically, the invention is an apparatus for sustaining an inductively coupled non-argon plasma discharge in a flowing gas at atmospheric pressure, and for dispersing sample for analysis in the plasma discharge for the purpose of elemental analysis of the sample by emission spectroscopy, the apparatus comprising in combination:

(a) a plasma discharge containment tube, the inner diameter of which is between about 13 to 25 mm; a coaxial intermediate tube which is recessed within the containment tube and forms an annulus therewith; a coaxial central tube which forms an annulus with the inner surface of the intermediate tube;

(b) an induction coil coaxially about the containment tube; a radio frequency power source of no less than about 27.12 MHz operatively connected to the induction coil; an electronic impedance controller circuit operatively connected between said power source and induction coil to automatically or manually match the impedance of the plasma discharge to the output impedance of the radio frequency power source;

(c) means supplying a non-argon gas or a mixture of gases not containing substantial argon, and connected through a variable flow controller to conduit means for supplying at separately controllable flow rates, non-argon plasma gas to the annulus between the central tube and intermediate tube, and non-argon coolant gas to the annulus between the containment tube and intermediate tube; the central tube communicating with a device for supplying flowing sample laden carrier gas for analysis;

(d) electrical means to initiate a primary plasma discharge; a detector comprising a spectrometer in optical communication with the plasma discharge, and suitable for emission spectroscopic analysis of the emitted light of the plasma resulting from sample dispersed in the plasma discharge;

(e) said apparatus further defined by a configuration factor in the range critically of between about 0.92 to $<1$, the configuration factor being effective to permit the plasma discharge to be moved and spaced sufficiently from contact with any surface of the containment and intermediate tubes to prevent detrimental plasma discharge induced ablation of any said tube surface.

GENERAL DISCUSSION

The basic apparatus includes a plasma torch consisting of three tubes, preferably concentric cylinders. The plasma discharge rests within the outermost (containment) cylinder inside the coil region and near the top of the two inner cylinders (the intermediate tube, and nebulizer or central tube). The central tube is used as a means of injecting aspirated solutions or sample powders into the plasma. The plasma desolvates, vaporizes, atomizes, and excites the elements contained within the aerosol droplets. These excited states, produced also with powders, emit radiation upon relaxation to the ground state.

When the induction coil is energized, a plasma discharge is preferably first initiated in flowing argon, whereupon a stable discharge results. Flowing air or other non-argon gas is then introduced and mixed with the argon while simultaneously cutting off and thus diluting the flow of argon. The eventually achieved non-argon plasma discharge is then sustained by the field of the coil after the starting conditions are established. The conversion follows the order of first converting the aerosol gas to a non-argon gas; then that of the inner annulus, and finally that of the outer annulus, hence resulting in a total air or non-argon ICP.

Direct starting or initiation of the air or non-argon plasma at atmospheric pressure is a procedure which generally requires more than a 27.12 MHz or 40.68 MHz induced induction field. The plasma is thus most easily initiated in a gas of low thermal conductivity and low ionization potential such as argon. It is also possible that a high-intensity induction field could cause ionization by the electrical breakdown of the high pressure gas, but possible breakdown of the air surrounding the coil or puncture of the cylinder material containing the gas owing to the high electric field strength makes such a starting method generally less desirable.

To avoid the above-mentioned problems with the apparatus used for the present invention, the plasma is accordingly first initiated in argon. More specifically, this is achieved by seeding the flowing gas with free electrons generated by a Tesla coil breakdown in the argon upstream from the energized coil. These electrons gain energy from the oscillating magnetic field and eventually acquire sufficient energy to ionize the flowing argon to the extent necessary to achieve a stable discharge. This process occurs rapidly (e.g., less than 100 ms.). To convert to a total non-argon air supported discharge from an argon discharge, air or non-argon gas, air is caused to replace the argon in the three passages of the plasma torch sequentially (as described) until all the argon is eliminated.

During the conversion, the tip of the intermediate tube may reach incandescence for a few seconds. Such incandescence seems to produce a smoother transition from one plasma to the other. It is thought that this may result in preheating the incoming gas sufficiently to allow rapid ionization of the air or non-argon gas by the magnetic field and the existing argon plasma. Such incandescence is one of a possible number of methods whereby said transition can be produced more rapidly and at lower power. Once the argon flow in the torch has been reduced to zero, an appropriate flow of air in the inner annulus will return the glowing tube to a condition where there is no further contact with the plasma.

Various materials can be used to make up the torch cylinders. Fused silica is used for the most common applications, while alumina, boron nitride, and graphite have also been substituted. For this invention, a combination of various materials is found to be advantageous but not necessary. Fused silica for the containment and intermediate tubes was adequate. Experimentation with intermediate tubes made of boron nitride or graphite resulted in some difficulties during generation of the air discharge.

Owing to the intense heat present during the transition stage, the central tube should be made of a highly thermal conducting material. In the case of this invention, the central tube consisted of a 4 cm length of boron nitride fitted into a 12 cm length of fused silica capillary tubing. The boron nitride resists physical distortion during intense heating and has the added advantage of being easily machinable.

Stabilization and containment of the air or non-argon ICP requires a critical modification in the design of the type of ICP torch commonly used for optical emission spectroscopy. To allow for changes in cylinders or material, a demountable torch was thus designed after the conventional Scott configuration. However, with the conventional torch, generation and stabilization of the air discharge was accompanied by ablation and destruction of the intermediate tube. Efforts to prevent the ablation entirely resulted in plasma instabilities or extinction. In contrast, operation of the air ICP in the modified torch with a configuration factor in this instance of 0.94–0.95 was possible over a reasonable power range without ensuing damage to the cylinders.

With and air discharge available, analysis of airborne particles now becomes more feasible. Analysis of suspended particles in ambient air can now be achieved by injection of the sample directly into a total air ICP. Such a method is preferred to that of injecting air into an argon ICP owing to the lack of ensuing instabilities and better detection capabilities. Introduction of powdered samples into a total air ICP results in more efficient decomposition of refractory compounds than when the same powder is injected into a total argon ICP. This is believed to be due to the higher thermal conductivity of air.

The basic apparatus for injecting powdered sample consists, e.g., of a chamber wherein the powdered sample is located. The chamber is equipped with a provision to cause the particles making up the powder to become airborne and thereby be swept away. A conventional pump which will not contaminate the sampled air is used to supply the air to the central tube of the torch. A damping chamber is inserted between the pump and the torch to eliminate pump pulsations. The pump has speed controls suitable to adjust the flow to a proper flow rate.

The damping chamber serves the additional purpose of mixing the particles with the surrounding air. This action results in an exponential dilution of the particles in the damping chamber as a function of time. Such as effect can be used to calibrate the entire system over a reasonable concentration range with only one standard sample.

It is, therefore, the objective of this invention to provide apparatus for starting, stabilizing, and containing a total air or non-argon ICP and the use of the non-argon ICP in elemental analysis including analysis of airborne particles.

IN THE DRAWINGS

FIG. 1 is a block diagram showing the physical makeup and layout of the entire instrument supporting the invention. Table I, contains a description of the original components used in said instrument.

FIG. 3 shows an embodiment of the invention adapted to the analysis of airborne particles.

DETAILED DESCRIPTION OF THE PREFERRED EMBODIMENT

Figure 2:
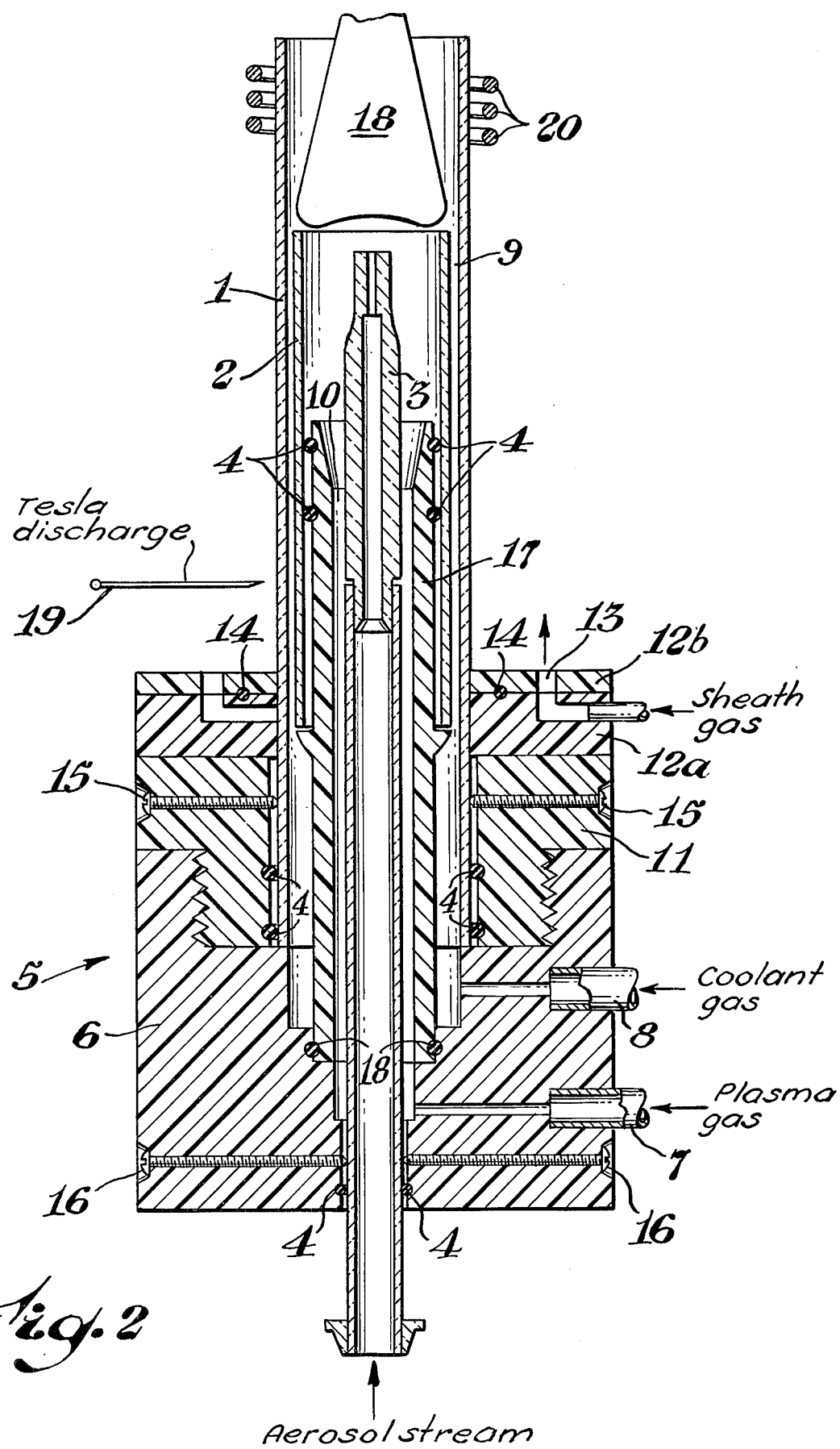
FIG. 2 is a schematic view, primarily in the vertical cross section of a preferred embodiment of the plasma torch element of the apparatus used for the present invention.

FIG. 2 shows a preferred embodiment of the torch. This is the demountable design where the quartz tubes, containment tube 1, intermediate tube 2, and central or nebulizer tube 3, are held in place by O-rings 4 in base 5. The base 5 is comprised of plastic body element 6 into which are machined a plasma gas inlet 7 and coolant inlet 8. The coolant inlet communicates with the outer annulus 9; whereas the plasma gas is supplied to the inner annulus 10 (between central tube 3 and intermediate tube 2). The coolant and plasma gas are admitted tangentially into each annulus 9, 10 according to convention.

The base 5 additionally is composed of a threadably detachable mounting ring 11; to the top of which ring 11 is attached a collar 12 defining an annular orifice 13. The collar 12 is machined of plastic components 12a and 12b and is attached, e.g., by metal screws to the mounting ring 11. An O-ring 14 serves to seal components 12a and 12b at the interface. Air or other sheath gas is supplied to annular orifice 13, and flows as a column up the sides of the containment tube 1 for the purpose of aiding plasma discharge stability. In servicing the torch, the containment tube 1, is demounted and replaced by loosening alignment screws 15; three in number and set apart by 120°. A second set of three alignment screws 16 permits the central tube 3 to be easily removed. The intermediate tube 2 is mounted on sleeve element 17, in turn, pressure fitted in body element 6 using O-rings 18; and thus, also may be demounted from base 5 and conveniently replaced.

Initiation of the plasma 18, the starting process is generally possible by use of a preliminary plasma generated in argon. In FIG. 2, the primary plasma (not shown) is initiated typically by the use of an auxiliary supply of electrons from a Tesla coil 19 or other similar device. These electrons are caught up by the electric field produced by an induction coil 20 energized by high frequency energy source 21. Power from the high frequency energy source 21 is delivered to the ICP discharge through tuning matchbox 22, or other equally effective circuit (see FIG. 1). Matchbox 22 is necessary for suitable power input whenever power from such a high frequency energy source is conducted to the load through a flexible transmission cable 23 of a given characteristic impedance.

The generation of a non-argon ICP is not limited to an RF generator operated at fixed frequency. A free-running generator would serve equally well, eliminating the need for matchbox 22 and simplifying the previously necessary tuning of critical components (since the equivalent of the matchbox circuit is supplied with a free running RF generator concept).

With sufficient power delivered to the induction coil 20 ion filaments inside the torch outer annulus are generated. These filaments form closed loops in the coil region allowing energy source 21 to couple more power to the electrons thereby generating a full plasma discharge. Conventional ICP torches can typically be ignited in the presence of only a coolant flow of argon. Ignition of an argon discharge with the modified torch is made easier when both coolant and plasma gas flow of argon gas are initially present.

At frequencies generally below about 54 MHz and using conventional crystal controlled generators for sustaining analytical ICP discharges, one way of generating molecular gas ICP discharges requires initially starting up in an argon ICP and changing over the gas flows from argon to the chosen molecular gas while simultaneously maintaining an impedance match between the plasma discharge and the RF generator.

More specifically, in an argon/non-argon or air conversion scheme, the apparatus includes dual gas supplies composed, e.g., of regulated compressed argon and air cylinders 24 and 25. The flow manifold 26 consists of rotameters, and flow and pressure regulators which permit plasma gas line 28, coolant line 27, aerosol line 29 and sheath gas line 30 to supply controlled gas flows. Generally, plasma line 28 is desirably operable between variable flow rates of 1-3 LPM; coolant line 27 of 15-30 LPM; aerosol line 29 of 0.5-2 LPM; and sheath line 0-15 LPM. Coolant line 27 is adjustably fed controlled mixtures of argon/non-argon gas during the conversion; whereas the plasma line 28 and aerosol line 29 are fed pure gases from their respective rotameters. The referred to conversion can be achieved in various ways, one of which is outlined below for operation of an ICP in total air at 27.12 MHz. These steps together with a description of the apparatus are presented in Table II.

TABLE I

Plasma Equipment Description

Inductively Coupled Plasma Source

| | |
|---|---|
| RF Generator | Lepel, Model T-10-3-MCl-X-SA 27.12 MHz, 0.2–10 kW |
| Transm. Cable | Coaxial RG 218/U, ¼ wavelength LC connector |
| Matchbox | Jennings, USC-500 Vacuum variable cap. 10–500 pF, 10 kV |
| | Jennings, USCB-100 Vacuum variable cap. 5–100 pF, 15 kV |
| Induction Coil | 3-turn, ⅛ in. copper, 25 mm diameter, water cooled |

Sample Aerosol Generation

| | |
|---|---|
| Nebulizer | Cross flow, 1.5 mL/min., 45 psi |
| Spray Chamber | Cylindrical, 150 mL |

Torch Assembly

| | |
|---|---|
| Base | Demountable, teflon, adjustable |
| Tubes | Quartz outer tube 18 mm i.d. |
| | Quartz intermediate tube about 17 mm o.d. |
| | Boron nitride tipped quartz aerosol tube, 0.8 mm orifice |

Gas Flow Controller

| | |
|---|---|
| Coolant (molecular gas) | Flow regulator, Brooks Instr. 8902 Rotameter, Brooks Instr. R-6-25-A |
| Coolant (argon) | Rotameter, Brooks Instr. R-6-25-B |
| Intermediate | Rotameter, Brooks Instr. R-2-15-B |
| Inner | Flow regulator, Brooks Instr. 8942 Rotameter, Brooks Instr. R-2-15-A |

Spectrophotometers

| | |
|---|---|
| Monochromators | 0.75 m Czerny-Turner Spex Model 1700II |
| Grating | 1200 lines/mm, 111 Å/mm |
| Slit Width | 5–130 micrometers |
| Slit Height | 2 mm entrance, 25 mm exit |

Optical Components

| | |
|---|---|
| Lens | Quartz, 2-in. diameter 200 mm fl., 1:1 image Oriel A-11-661-37 |

TABLE II

PROCEDURE FOR CONVERTING AN ARGON ICP INTO A MOLECULAR GAS ICP DISCHARGE

| | Gas Flow Rates (LPM) | | | | | | Capacitor Settings Capacitance (pF) | | Power | |
|---|---|---|---|---|---|---|---|---|---|---|
| | Coolant | | Plasma | | Aerosol | | | | For. | Rev. |
| Step # | Ar | Air | Ar | Air | Ar | Air | $C_1$ | $C_2$ | (kw) | (w) |
| 1 | 14 | 0 | 1.5 | 0 | 1.0 | 0 | 75 | 350 | 1.0 | 5 |
| 2 | 14 | 0 | 1.5 | 0 | 0 | 0.1 | 72 | 380 | 0.9 | 50 |
| 3 | 14 | 0 | 1.5 | 0 | 0 | 0 | 70 | 400 | 0.8 | 100 |
| 4 | 14 | 0 | 0 | 1.5 | 0 | 0 | 66 | 430 | 1.5 | 150 |
| 5 | 14 | 5 | 0 | 1.5 | 0 | 1.0 | 66 | 430 | 2.0 | 125 |
| 6 | 10 | 10 | 0 | 1.5 | 0 | 1.0 | 66 | 430 | 3.5 | 100 |
| 7 | 0 | 20 | 0 | 1.5 | 0 | 1.0 | 66 | 430 | 3.5 | 50 |

Once initiation has produced a stable argon plasma discharge, plasma and aerosol gas lines 28 and 29 can be purged of argon and filled with air supplied by the compressed air cylinder. Flowing air is now allowed to mix with the argon in the outer annulus. The eventual maximum flow of air in the outer annulus is then introduced while the flow of argon is simultaneously reduced. During this step, the discharge becomes thermally pinched giving the visual appearance of being compressed lower down in the torch. As the discharge makes close contact with the top of the quartz intermediate tube, this tube heats and glows incandescently. Almost coincident with this incandescence the discharge becomes considerably less intense and longer in length than is normally apparent if only argon gas were present. This indicates that the discharge has changed from an argon-dominated discharge to a discharge dominated by the thermal and electrical properties of air. At this stage all the argon reaching the torch can be eliminated while flow of air in the intermediate tube is increased until the incandescence of the quartz intermediate tube is no longer apparent, and the tube returns to a normal operating state. Final stabilization is accomplished by optimizing the flows present in all three cylinders.

With the present apparatus, retuning of the critical components was necessary when performing the transition from the argon plasma to the air plasma. This is a result of the difference in electrical properties of the various plasmas producing changes in the electrical load. Whereas matchbox 22 required manual adjustment of the internal components, tuning matchboxes exist in which such tuning is performed automatically through feed back circuitry. A total air ICP discharge for spectrochemical analysis has been successfully generated with both manually and automatically tuned systems. All illustration of this embodiment operated with automatic impedance matching at higher frequency is given below.

The plasma torch of FIG. 2 has been operated with an 18 mm diameter quartz tube with a three turn solenoid (induction) coil of ⅛ inch diameter water cooled copper tubing having a spacing of 3/32 inch between turns. Coil 20 is connected to a commercial (Lepel) 10 kW, 13.56 MHz generator modified to operate at 27.12 MHz. The power delivered to the plasma has not been measured directly, however, indirect evidence indicates that about 80 percent of the power leaving the generator is delivered to the plasma. The power necessary to generate a discharge in the torch varies with the gas used to sustain it and the frequency of the rf generator. With the torch of FIG. 2, plasmas for spectrochemical analysis have been sustained in which the collective flow in all three tubes was argon, nitrogen, oxygen, air, or as much as 95 percent helium. Argon supported discharges with the central gas flows of pure argon, nitrogen, oxygen, air or helium have also been used for spectrochemical application. Also, air supported discharges with central gas flows of pure argon, nitrogen, oxygen or helium can be operated for such purposes. Similar results can be obtained with a prefabricated torch of fixed dimensions.

The total air ICP has been operated at 27.12 MHz at a minimum power of 1.8 kW and a maximum power of 6 kW with the above described high frequency energy source. With rf equipment capable of maintaining a higher overpotential on the induction coil while attempting to initiate a primary plasma, an ICP can be generated directly in the molecular gas, circumventing the previously necessary step of starting in argon.

The following experimental data was developed using 0.75 meters Czerny-Turner spectrometer 31 with a picoammeter read-out 32. The spectrometer 31 is in optical communication with the plasma discharge 18 via a lens (33) located at a focal point of 30 cm from the plasma discharge and spectrometer entrance slit. The plasma was viewed at an observation height varying from 3 to 10 mm above the top winding of the induction coil 20.

Solution (35), used for this set of data were aspirated into the plasma via solution feed tube 35 through the central tube 3 using a conventional cross-flow pneumatic nebulizer 34 and cylindrical spray chamber 37.

A comparison of the total argon discharge with the total air discharge for the analysis of various elements in solution form is presented in Table III.

TABLE III
COMPARISON OF DETECTION LIMITS FOR VARIOUS ELEMENTS AS DETERMINED BY NITROGEN AND AIR ICP DISCHARGES

| Element | Wavelength NM | Difficulty of Excitation* EV | Detection Limit Ng/mL Air | Argon (wavelength)** |
|---|---|---|---|---|
| MN I | 403,076 | 3.0 | 27 | 44 |
| CA II | 393,366 | 9.2 | 0.2 | 0.2 |
| Al I | 396,152 | 3.1 | 35 | 28 |
| EU I | 397,196 | 3.1 | 40 | 9.4 |
| LA I | 624.9 | 1.9 | 800 | 10(379.4NM) |
| BA I | 553.5 | 2.2 | 100 | 81(489.9NM) |
| II | 455,403 | 7.9 | 1.3 | 1.3 |
| NA I | 588,995 | 2.1 | 0.72 | 29 |
| CS I | 852.1 | 1.4 | 80 | 42000(452.6NM) |
| RB I | 780.0 | 1.6 | 94 | 37000(420.1NM) |

*Ionization Energy + Excitation Energy = Difficulty of Excitation
**Taken from Winge, R. K., Peterson, V. J., Fassel, V. A., Applied Spectroscopy, 33(3), 209, 1979.

The detection limits reported in Table III were calculated from the ratio of the net signal to the background signal for a specific concentration of the element assuming three times the relative standard deviation of the background signal. The background signal was measured in all cases in the absence of the element and was an indication of the amount of continuum radiation present at the wavelength utilized.

Similar experiments were carried out on a commercial (PLASMA THERM, INC.) 5 kw, 40.68 MHz energy source with the same coil configuration. A description of the components used in this example is given in Table IV.

Generation of a molecular gas (specifically air) ICP was accomplished using the conversion details previously given. These steps are summarized in Table V.

TABLE IV

| | Equipment |
|---|---|
| RF power source | Plasma Therm, Inc. MD1 HF15000D |
| Transmission Line | Andrew Corp., Heliax, LDF5-50 |
| Automatic Independance Matching system | Plasma Therm, Inc. MD1 AMN-PS-1 |
| Induction Coil | Copper, ¼" dia. silver plated, 3 turn |
| Torch | 18 mm i.d. of outer tube, 3 concentric tubes; configuration factor, 0.944 |
| Gas Controller | |

TABLE IV-continued

| | Equipment |
|---|---|
| Outer Stream | 0–25 LPM; 2 rotameters, Porter Instrument Co. A-250-5 (steel ball). Provides for mixing of gases in this stream. |
| Intermediate | 0–5 LPM; rotameter, Porter Instrument Co., A-250-3 (saphire ball). Provides for either/or control of gas in this stream. |
| Inner | 0–2.5 LPM; Rotameter, Porter Instrument Co., A-157-2 (steel ball). Provides for either/or control of gas in this stream. |

TABLE V
Procedure for Conversion from an Argon ICP to a Non-argon ICP at 40.68 MHz

| | Gas Flow Rates | | | | | | Capacities Settings (pF) | | Power | |
|---|---|---|---|---|---|---|---|---|---|---|
| | Outer | | Intermediate | | | | | | | |
| | Ar | Air | Ar | Air | Ar | Air | C (series) | C (shunt) | For. (kw) | Rev. (w) |
| 1 | 14 | 0 | 1.0 | 0 | 1.0 | 0 | 75 | 87 | 1.0 | 10 |
| 2 | 14 | 0 | 0.5 | 0 | 0 | 1.0 | 75 | 90 | 1.0 | 10 |
| 3 | 14 | 0 | 0.5 | 0 | 0 | 0 | 75 | 110 | 1.0 | 10 |
| 4 | 14 | 0 | 0 | 0.5 | 0 | 0 | 75 | 130 | 1.5 | 10 |
| 5 | 10 | 5 | 0 | 0.5 | 0 | 1.0 | 75 | 146 | 1.5 | 10 |
| 6 | 5 | 16 | 0 | 1.0 | 0 | 1.0 | 75 | 146 | 1.5 | 10 |
| 7 | 0 | 20 | 0 | 1.2 | 0 | 1.0 | 75 | 146 | 1.5 | <10 |

This method yielded an analytical air ICP discharge at a minimum power of 850 watts and a maximum power of 4.5 kw. Total nitrogen and total oxygen discharges for spectrochemical analysis could also be sustained with as little as 1.5 kw forward power.

FIG. 3 shows a system designed for analysis of pulverized powders using the total air ICP. Sampling chamber 38 allows for changing the sample reservoir 39 through the hinged front panel 40. A ½ inch hole on the top of chamber 38 is fitted with an externally activated squeeze bulb device 41 which through extended nozzle portion 42 reproducibly caused the powder in the sample reservoir 39 to be suspended in the moving air. In one version this device consisted simply of a rubber bulb of 50 mL volume which upon depression yields a controlled blast of air directed down onto the powder located in reservoir 39. This in turn caused small particles to become suspended in the air. These particles are swept towards a collection funnel 43 by the draft of air from an inlet 44 communicating with filtered room air through valve 47. This draft of air arises from the negative pressure imposed on the sampling chamber 38 by a paristalic pump 46 through valve 47.

After the disturbance created by device 41 is completed, further sampling from the chamber is terminated by rerouting the flow of air around sampling chamber 38 by changing valves 45 and 47. This allows the user to either change the sample or allow the proper settling time before a subsequent sampling is performed. Pump 46 causes air to be drawn through chamber 38 as well as provides a sufficient pressure for a central air flow rate to the torch from 0.3 to 2 liter per minute. To eliminate the flow pulsations produced by pump 46, a damping chamber 48 is installed between pump 46 and the nebulizer tube 3 of the plasma torch.

An important feature of the addition of chamber 48 to the system is that calibration of signal intensity as a function of analyte concentration is now greatly simplified. Otherwise, tedious calibrations using multiple standards would be required. The mentioned simplified approach is possible due to the exponential behavior of the dilution of sample with air as a function of time in the damping chamber 48. By knowing the original concentration, the air flow rate and damping chamber volume, the operator can record the logarithm of the emission signal as a linear function of time which can be then correlated with a calculated analyte concentration. Exponential dilution has been used for calibration purposes in the field of gas chromatography. Use of this method in the analysis of powders by ICP-AES has not been before documented.

A typical set of data taken with the apparatus of FIG. 3 as set out in Table VI.

TABLE VI

| | |
|---|---|
| Outer Flow | 20 LPM |
| Intermediate Flow | 1.3 LPM |
| Central Flow | 0.96 LPM |
| Power | 3.5 kW |
| Signal Intensity, Amperes, 33% CaO | $5.68 \times 10^{-7}$ |
| Background Intensity, Amperes, 33% CaO | $2 \times 10^{-10}$ |
| Signal/Background 33% CaO | 2840 |
| Detection Limit, ng/m$^3$ | 30 |
| Signal Intensity, Amperes, 2% CaO | $2.2 \times 10^{-7}$ |
| Background Intensity, Amperes, 2% CaO | $2 \times 10^{-10}$ |
| Signal/Background, 2% CaO | 1100 |
| Slope, Amperes % | $8.2 \times 10^{-9}$ |

It will be apparent to those skilled in the art that the basic apparatus of the present invention may be modified by mechanical changes such as streamlining the torch, by automating the impedance matching device, by replacing device 41 with a pneumatic jet, or by using a pump other than a peristaltic pump for supply of the central air flow to the torch through the sample chamber. It should be understood that modifications of this nature are intended to be within the scope of this invention, if not literally, then by the Doctrine of Equivalents by which the inventors state their intent to rely in construction of the scope of their claimed invention below.

Statement of Intent

The inventors hereby state their intent to rely on the Doctrine of Equivalents to determine and assess the fair scope of their invention as set out and defined in the following claims 1-10.

What is claimed is:

1. Apparatus for sustaining an inductively coupled non-argon plasma discharge in a flowing gas at atmospheric pressure, for dispersing sample for analysis in the plasma discharge, and for elemental analysis of the sample by emission spectroscopy, the apparatus comprising in combination:
   (a) a plasma discharge containment tube, the inner diameter of which is between about 13 to 25 mm; a coaxial intermediate tube which is recessed within the containment tube and forms an annulus therewith; a coaxial central tube which forms an annulus with the inner surface of the intermediate tube;
   (b) an induction coil coaxially about the containment tube; a radio frequency power source of no less than about 27.12 MHz operatively connected to the induction coil; an electronic impedance controller circuit operatively connected between said power source and induction coil to automatically or manually match the impedance of the plasma discharge to the output impedance of the radio frequency power source;
   (c) means supplying a non-argon gas or a mixture of gases not containing substantial argon, and connected through a variable flow controller to conduit means for supplying at separately controllable flow rates, non-argon plasma gas to the annulus between the central tube and intermediate tube, and non-argon coolant gas to the annulus between the containment tube and intermediate tube, the gases being admitted tangentially to each said annulus; the central tube communicating with a device for supplying flowing sample laden carrier gas for analysis;
   (d) electrical means to initiate a primary plasma discharge; a detector comprising a spectrometer in optical communication with the plasma discharge, and suitable for emission spectroscopic analysis of the emitted light of the plasma resulting from sample dispersed in the plasma discharge;
   (e) said apparatus further defined by a configuration factor in the range critically of between about 0.92 to <1, the configuration factor being effective to permit the plasma discharge to be moved and spaced sufficiently from contact with any surface of the containment and intermediate tubes to prevent detrimental plasma discharge induced ablation of any said tube surface.

2. The apparatus of claim 1 wherein the plasma gas is air.

3. The apparatus of claim 2 wherein the coolant gas is air, and wherein the gas supplying means is an air compressor.

4. The apparatus of claim 1 wherein the configuration factor is in the range between about 0.94 to <1.

5. The apparatus of claim 1 including an orifice about the containment tube to form a sheath gas column thereabout.

6. The apparatus of claim 1 wherein the containment tube is between about 13-18 mm I.D., and wherein the configuration factor is in the range between about 0.94 to <1.

7. The apparatus of claim 1 wherein the plasma gas is predominately oxygen, nitrogen or carbon dioxide.

8. The apparatus of claim 7 wherein the coolant gas is predominately oxygen, nitrogen or carbon dioxide.

9. The apparatus of claim 1 including a vessel of argon operatively connected to the inner annulus, outer annulus, and central tube for initiating a non-argon plasma.

10. The apparatus of claim 1 wherein the device for supplying sample laden carrier gas to the central tube comprises a device for supplying suspended powders.

* * * * *